(12) United States Patent
Emerson

(10) Patent No.: US 8,738,398 B1
(45) Date of Patent: May 27, 2014

(54) METHODS AND APPARATUS FOR IMPROVING HEALTHCARE

(75) Inventor: Erik Emerson, Pleasanton, CA (US)

(73) Assignee: Symplmed Pharmaceuticals, LLC, Cincinnati, OH (US)

( * ) Notice: Subject to any disclaimer, the term of this patent is extended or adjusted under 35 U.S.C. 154(b) by 56 days.

(21) Appl. No.: 13/284,423

(22) Filed: Oct. 28, 2011

Related U.S. Application Data

(60) Provisional application No. 61/408,560, filed on Oct. 29, 2010.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ........................................................ 705/2–3
See application file for complete search history.

(56) References Cited

U.S. PATENT DOCUMENTS

| | | | |
|---|---|---|---|
| 2003/0225595 A1* | 12/2003 | Helmus et al. | 705/2 |
| 2006/0218011 A1* | 9/2006 | Walker et al. | 705/3 |
| 2008/0001735 A1* | 1/2008 | Tran | 340/539.22 |
| 2009/0106313 A1* | 4/2009 | Boldyga | 707/104.1 |

* cited by examiner

*Primary Examiner* — Minnah Seoh
(74) *Attorney, Agent, or Firm* — Lange IP Law

(57) ABSTRACT

The present disclosure provides methods and apparatus for obtaining and using outcome information associated with a prescription drug. In an embodiment, doctors and patients are registered in a central prescription distribution system. Preferably, drugs prescribed using the central prescription distribution system are only available through the system and are shipped from one or more distribution hubs directly to the patient. Outcome data is collected from the patients in the system and used in a variety of ways.

21 Claims, 18 Drawing Sheets

FIG. 6

SystemX.com

SystemX.com

| Home | Account Settings | My Health | Essential Health Tips |

My Health
Welcome back, John!  (Log out)

Submit New Health Information

Date: [   ]
Blood Pressure: [   ] over [   ]
Weight: [   ]
Exercise Time: [hh:mm]

Diet:
☐ Chicken
☐ Beef
☐ Fish/Seafood
☐ Vegetables
☐ Fruits
☐ Diary
☐ Grains (Cereal, Bread, Etc.)

Comments: [            ]

Helpful Links... [▶]

(Reset) (Submit)

— 602

Latest Updates
as of October 31, 2010

Search for Records: 🔍 [        ] (Search)

| Date | Blood Pressure | Weight | Exercise Time | Drug | Diet | More Details |
|---|---|---|---|---|---|---|
| October 30, 2010 | 120/80 | 167 lb | 0:45 | DrugX | Fish, Beef... | Click here to view details |
| October 28, 2010 | 130/80 | 167 lb | 1:30 | DrugX | Salad, Ice Cream, Fruit... | Click here to view details |
| October 25, 2010 | 100/70 | 167 lb | 0:25 | DrugX | Rice, Pasta, Salad... | Click here to view details |
| October 24, 2010 | 150/90 | 167 lb | 0:00 | DrugX | Beef, Salad, Fruit... | Click here to view details |
| October 23, 2010 | 125/85 | 167 lb | 0:15 | DrugX | Salad, Ice Cream, Beef... | Click here to view details |
| October 16, 2010 | 122/90 | 167 lb | 1:30 | DrugX | Salad, Chicken, Fruit... | Click here to view details |
| October 14, 2010 | 120/80 | 167 lb | 2:52 | DrugX | Chicken, Beef, Fruit... | Click here to view details |

List All Records                              ▽ Page [1] of 3  △

| Patient | Rx | Days on Rx | Blood Pressure | Events |
|---|---|---|---|---|
| 1 | DrugX | 30 | Increased | Stroke |
| 2 | DrugX | 180 | Same | None |
| 3 | DrugX | 365 | Reduced | None |
| 4 | DrugX | 548 | Same | Cardiac Arrest |
| 5 | DrugX | 730 | Same | None |
| 6 | DrugY | 45 | Same | None |
| 7 | DrugY | 90 | Same | None |
| 8 | DrugY | 220 | Reduced | None |
| 9 | DrugY | 630 | Reduced | None |
| 10 | DrugY | 710 | Reduced | None |

Enrollment and Agreement Form

Prescriber Information

First Name _____ Middle Initial _____ Last Name _____ Suffix _____

Specialty _____ Name of Facility _____ Office Contact _____

Address _____ City _____ State _____ ZIP _____

E-mail _____ Phone (___) _____ Fax (___) _____

State License # _____ NPI # _____ DEA # _____

Prescriber Agreement

By signing below you agree to...

Prescriber Signature _____ Date _____

FIG. 18

Patient Enrollment / Prescription

Patient Information (PLEASE PRINT)

First Name: _____ Middle Initial: _____ Last Name: _____
Address: _____ City: _____ State: _____ ZIP: _____
Birthdate: __ / __ / __  Gender: ☐ M ☐ F  Preferred Time to Contact: ☐ Day ☐ Evening
Preferred Phone: (___)_____ Alternate Phone: (___)_____ E-mail: _____
Alternate Contact Name: _____ Phone: (___)_____ Relationship: _____

Insurance Information (PLEASE PRINT)

Insurance 1: _____ Policy Number: _____
Insurance 2: _____ Policy Number: _____

Fax or e-mail all patient insurance information, including drug benefit cards, to: X-XXX-XXX-XXXX or xxx@abcmedinc.com Patient/Guardian Signature: _____ Date: _____

Prescriber Information (PLEASE PRINT)

Office Contact: _____ E-mail: _____
First Name: _____ Last Name: _____ State License #: _____
Address: _____ City: _____ State: _____ ZIP: _____
Phone: (___)_____ Fax: (___)_____ NPI #: _____ DEA #: _____

Prescription

| Medication | Dose/Strength, mg | Pill Count # | Refills |
|---|---|---|---|
| ☐ DrugA | 3.5/2.5  7/5  14/10 | 30  90 | 0 1 2 3 4 5 6 |
| ☐ DrugB | 2  4  8 | 30  90 | 0 1 2 3 4 5 6 |
| ☐ DrugX | 10/12.5  20/12.5 | 30  90 | 0 1 2 3 4 5 6 |
| ☐ DrugY | 2.5/10  5/10  5/20  10/20 | 30  90 | 0 1 2 3 4 5 6 |
| ☐ DrugZ | 50/25  100/25 | 30  90 | 0 1 2 3 4 5 6 |

Instructions: _____

Ship to:
Name: _____ Address: _____
City: _____ State: _____ ZIP: _____ Phone: (___)_____

Prescriber Signature: _____ Date: _____

METHODS AND APPARATUS FOR IMPROVING HEALTHCARE

TECHNICAL FIELD

The present application relates in general to improving healthcare and more specifically to obtaining and using outcome information associated with the distribution of a prescription drug.

BACKGROUND

In the current prescription drug system, patients typically fill prescriptions at a retail pharmacy or by mail order. However, due to the need for patient involvement in completing the process of filling prescriptions, such as for example, inconvenience of waiting for the pharmacy to obtain the drug, traveling to the pharmacy, submitting a mail order prescription, the high cost of the drugs, and other factors, many prescriptions are never filled.

In addition, once the drugs are prescribed, there may be no tracking as to whether the prescription is filled, and/or no outcome data or transparency as to the efficacy of the drugs. Doctors, patients, and insurers are unable to compare the effectiveness of different drugs on different types of patients.

SUMMARY

In an embodiment, the present system provides methods and apparatus for obtaining and using outcome information associated with a prescription drug. In an embodiment, doctors and patients are registered in a central prescription distribution system. Preferably, drugs prescribed using the central prescription distribution system are only available through the system. In an embodiment, the development, prescription, and distribution of drugs as well as payment for same are vertically integrated.

Preferably, drugs prescribed using the central system are shipped from one or more distribution hubs directly to the patient. Because the drugs are shipped directly to the patient in response to a doctor's prescription with no retail middleman, patients do not have to travel to a pharmacy, prices are reduced, and fulfillment percentages increase.

In an embodiment, outcome data is collected from the patients in the system. For example, if the prescription is for hypertension, the patient may provide periodic blood pressure readings. The outcome data may be used, for example, to supply reports to doctors, payers, patients, government agencies, a health care plan, managed care organizations, etc. In addition, the outcome data may be used to influence compliance and/or adherence of the drug, select another prescription, develop another drug, refine or modify indications and/or market drugs.

In an embodiment, a method of monitoring an outcome associated with a prescription drug is disclosed. The method includes storing doctor registration information received from a doctor and receiving prescription data from the doctor. The prescription data being indicative of (i) the prescription drug, the prescription drug being approved for distribution by a government agency for an indicated medical condition, and (ii) a patient. The method also includes storing patient registration information received from at least one of the doctor and the patient an verifying the doctor is registered by accessing the doctor registration information in response to receiving the prescription data. If the doctor is registered, the method facilitates providing the prescription drug to the patient and storing outcome information received from at least one of the doctor and the patient. In this embodiment, the outcome information is associated with the patient and the indicated medical condition.

Receiving the prescription data from the doctor may occur before storing the patient registration information, after storing the patient registration information, and/or at substantially the same time as storing the patient registration information. Providing the prescription drug to the patient may include automatically shipping the prescription drug, automatically shipping the prescription drug a plurality of different times, providing the prescription drug directly to the patient, and/or providing the prescription drug to a registered location. The registered location may be a pharmacy. In one aspect, a type associated with the outcome information is predetermined based on the indicated medical condition.

In another aspect, a query is received and a report, based on the outcome information, is delivered in response to the query. The query may come from a doctor, a payer, a patient, a government agency, a health care plan, and/or a managed care organization. The report may include a comparison between two different prescription drugs. In another aspect, an outcome data collection device may be provided to the patient. Storing the doctor registration information, the patient registration information, and/or the outcome information is not mandated by the government agency. The prescription drug may not be available at any retail location via distribution from a manufacturer of the prescription drug.

In one aspect, over 90% of doctors allowed to prescribe the prescription drug are registered in a centrally accessible system. In another aspect, every doctor allowed to prescribe the prescription drug is registered in a centrally accessible system. In one aspect, over 90% of patients allowed to take the prescription drug are registered in a centrally accessible system. In another aspect, every patient allowed to take the prescription drug is registered in a centrally accessible system.

The outcome data may be used for influencing at least one of compliance and adherence of the prescription, selecting a different medical prescription, developing a different prescription drug, and/or marketing prescription drugs. In one aspect, outcome information associated with the patient and a prescribed medical device is stored. In one aspect, payment from a payer to a patient and/or a drug company for at least a portion of the prescription drug is facilitated.

In another embodiment, an apparatus for monitoring an outcome associated with a prescription drug is disclosed. The apparatus stores doctor registration information received from a doctor and stores prescription data from the doctor. The prescription data being indicative of (i) the prescription drug, the prescription drug being approved for distribution by a government agency for an indicated medical condition, and (ii) a patient. The apparatus also stores patient registration information received from a doctor and/or a patient and verifies the doctor is registered by accessing doctor registration information in response to receiving prescription data. If the doctor is registered, the apparatus facilitates providing the prescription drug to the patient and storing outcome information received from the doctor and/or the patient. In this embodiment, the outcome information is associated with the patient and the indicated medical condition.

In yet another embodiment, a computer readable memory storing software instructions is structured to cause a processor store doctor registration information received from a doctor and store prescription data from the doctor. The prescription data being indicative of (i) the prescription drug, the prescription drug being approved for distribution by a government agency for an indicated medical condition, and (ii) a patient. The processor also stores patient registration information received from a doctor and/or a patient and verifies the doctor is registered by accessing doctor registration information in response to receiving prescription data. If the doctor is registered, the processor facilitates providing the prescription drug to the patient and storing outcome information received from the doctor and/or the patient. In this embodiment, the outcome information is associated with the patient and the indicated medical condition.

Additional features and advantages are described herein, and will be apparent from the following Detailed Description and the figures.

BRIEF DESCRIPTION OF THE FIGURES

FIG. 6 is a screen shot of an example of a patient dashboard.

FIG. 8 is an example of a drug comparison chart.

FIG. 9 is a screen shot of an example patient entry and prescription application.

FIG. 10 is a screen shot of an example outcome data collection application.

FIG. 17 is an example of a doctor registration form.

FIG. 18 is an example of a prescription/patient registration form.

DETAILED DESCRIPTION

Figure 1:
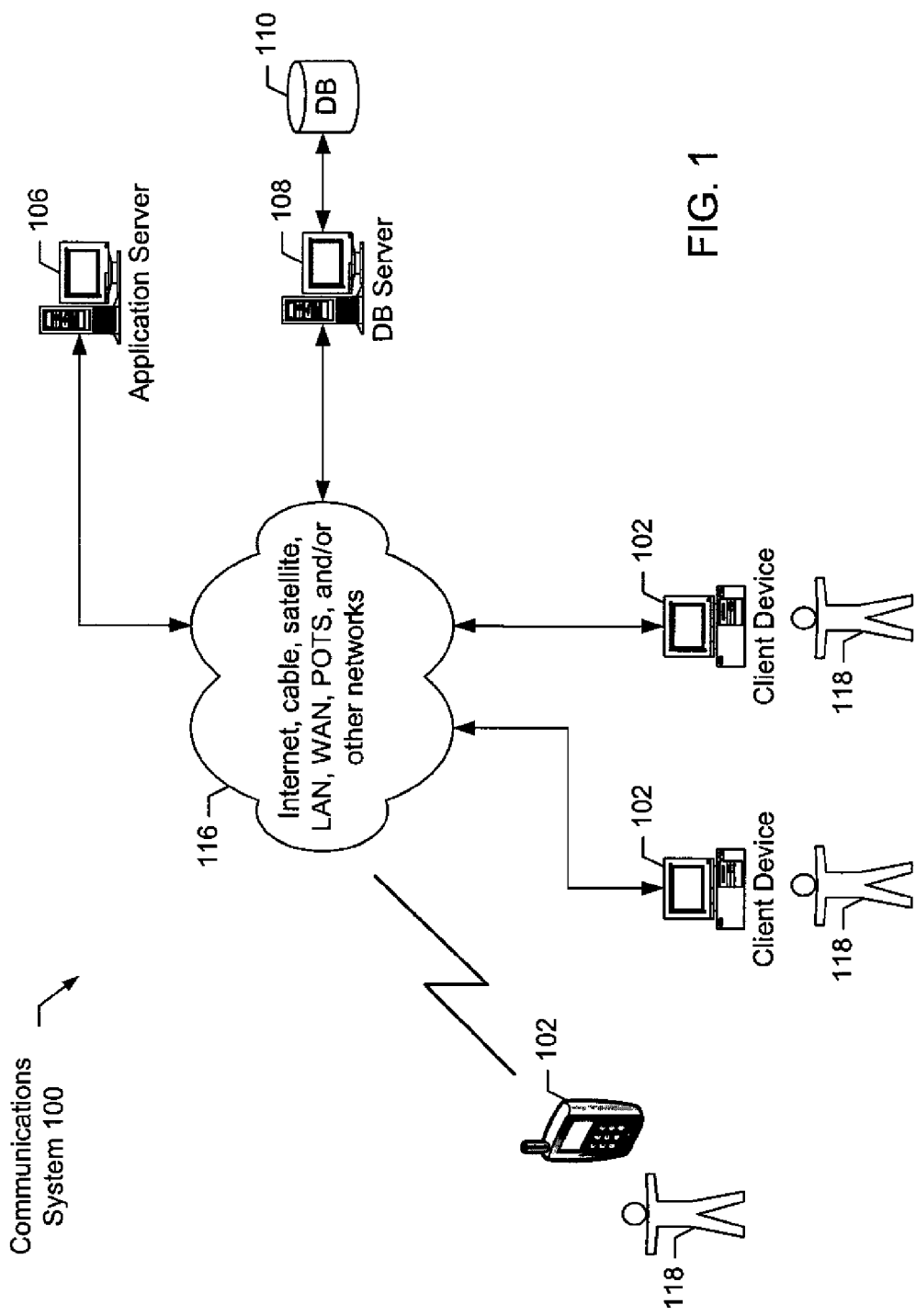
FIG. 1 is a high level block diagram of an example communications system.

The present system is most readily realized in a network communications system. A high level block diagram of an exemplary network communications system 100 is illustrated in FIG. 1. The illustrated system 100 includes one or more client devices 102, one or more application servers 106, and one or more database servers 108 connected to one or more databases 110. Each of these devices may communicate with each other via a connection to one or more communications channels 116. The communications channels 116 may be any suitable communications channels 116 such as the Internet, cable, satellite, local area network, wide area networks, telephone networks, etc. It will be appreciated that any of the devices described herein may be directly connected to each other and/or connected over one or more networks.

One application server 106 may interact with a large number of client devices 102. Accordingly, each application server 106 is typically a high end computing device with a large storage capacity, one or more fast microprocessors, and one or more high speed network connections. Conversely, relative to a typical application server 106, each client device 102 typically includes less storage capacity, less processing power, and a slower network connection.

Figure 2:
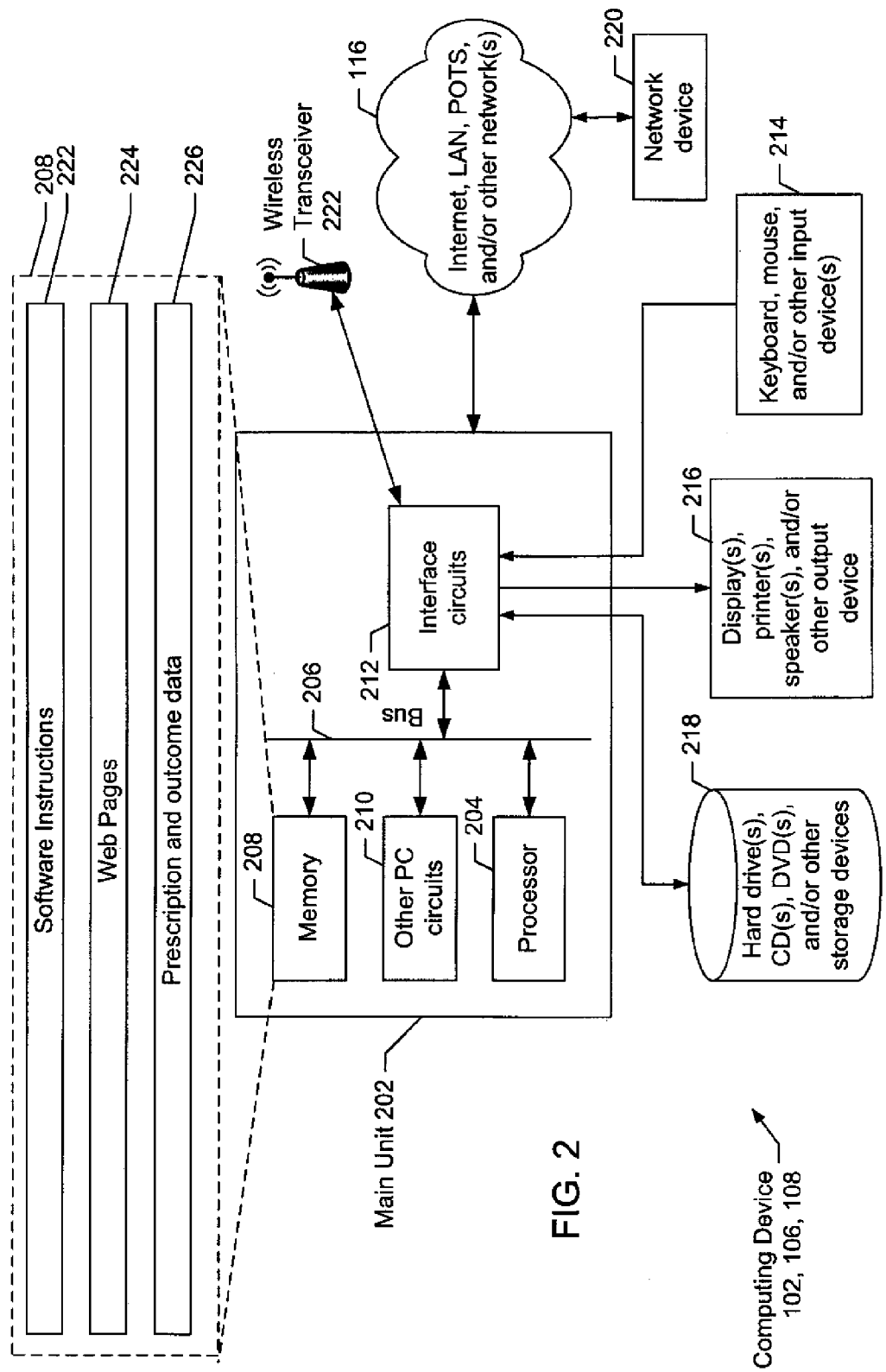
FIG. 2 is a more detailed block diagram showing one example of a computing device.

A detailed block diagram of an example computing device 102, 106, 108 is illustrated in FIG. 2. Each computing device 102, 106, 108 may include a server, a desktop computer, a laptop computer, a tablet computer, a personal digital assistant (PDA), a smart phone, and/or any other suitable computing device. Each computing device 102, 106, 108 preferably includes a main unit 202 which preferably includes one or more processors 204 electrically coupled by an address/data bus 206 to one or more memory devices 208, other computer circuitry 210, and one or more interface circuits 212. The processor 204 may be any suitable microprocessor.

The memory 208 preferably includes volatile memory and non-volatile memory. Preferably, the memory 208 and/or another storage device 218 stores software instructions 222 that interact with the other devices in the system 100 as described herein. These software instructions 222 may be executed by the processor 204 in any suitable manner. The memory 208 and/or another storage device 218 may also store one or more data structures, digital data indicative of documents, files, programs, web pages, etc. retrieved from another computing device 102, 106, 108 and/or loaded via an input device 214.

The example memory device 208 stores software instructions 222, web pages 224, and prescription and outcome data 226 for use by the system as described in detail below. It will be appreciated that many other data fields and records may be stored in the memory device 208 to facilitate implementation of the methods and apparatus disclosed herein. In addition, it will be appreciated that any type of suitable data structure (e.g., a flat file data structure, a relational database, a tree data structure, etc.) may be used to facilitate implementation of the methods and apparatus disclosed herein.

The interface circuit 212 may be implemented using any suitable interface standard, such as a Bluetooth interface, an Ethernet interface and/or a Universal Serial Bus (USB) interface. One or more input devices 214 may be connected to the interface circuit 212 for entering data and commands into the main unit 202. For example, the input device 214 may be a keyboard, mouse, touch screen, track pad, track ball, isopoint, and/or a voice recognition system.

One or more displays, printers, speakers, and/or other output devices 216 may also be connected to the main unit 202 via the interface circuit 212. The display 216 may be a cathode ray tube (CRTs), liquid crystal displays (LCDs), or any other type of display. The display 216 generates visual displays of data generated during operation of the computing device 102, 106, 108. For example, the display 216 may be used to display web pages received from the application server 106. The visual displays may include prompts for human input, run time statistics, calculated values, data, etc.

One or more storage devices 218 may also be connected to the main unit 202 via the interface circuit 212. For example, a hard drive, CD drive, DVD drive, flash memory drive, and/or other storage devices may be connected to the main unit 202. The storage devices 218 may store any type of data used by the computing device 102, 106, 108.

Each computing device 102, 106, 108 may also exchange data with other computing devices 102, 106, 108 and/or other network devices 220 via a connection to the communication channel(s) 116. The communication channel(s) 116 may be any type of network connection, such as an Ethernet connection, WiFi, WiMax, digital subscriber line (DSL), telephone line, coaxial cable, etc. Users 118 of the system 100 may be required to register with the application server 106. In such an instance, each 118 user may choose a user identifier (e.g., e-mail address) and a password which may be required for the activation of services. The user identifier and password may be passed across the communication channel(s) 116 using encryption built into the user's browser, software application, or computing device 102, 106, 108. Alternatively, the user identifier and/or password may be assigned by the application server 106.

Figure 3A:
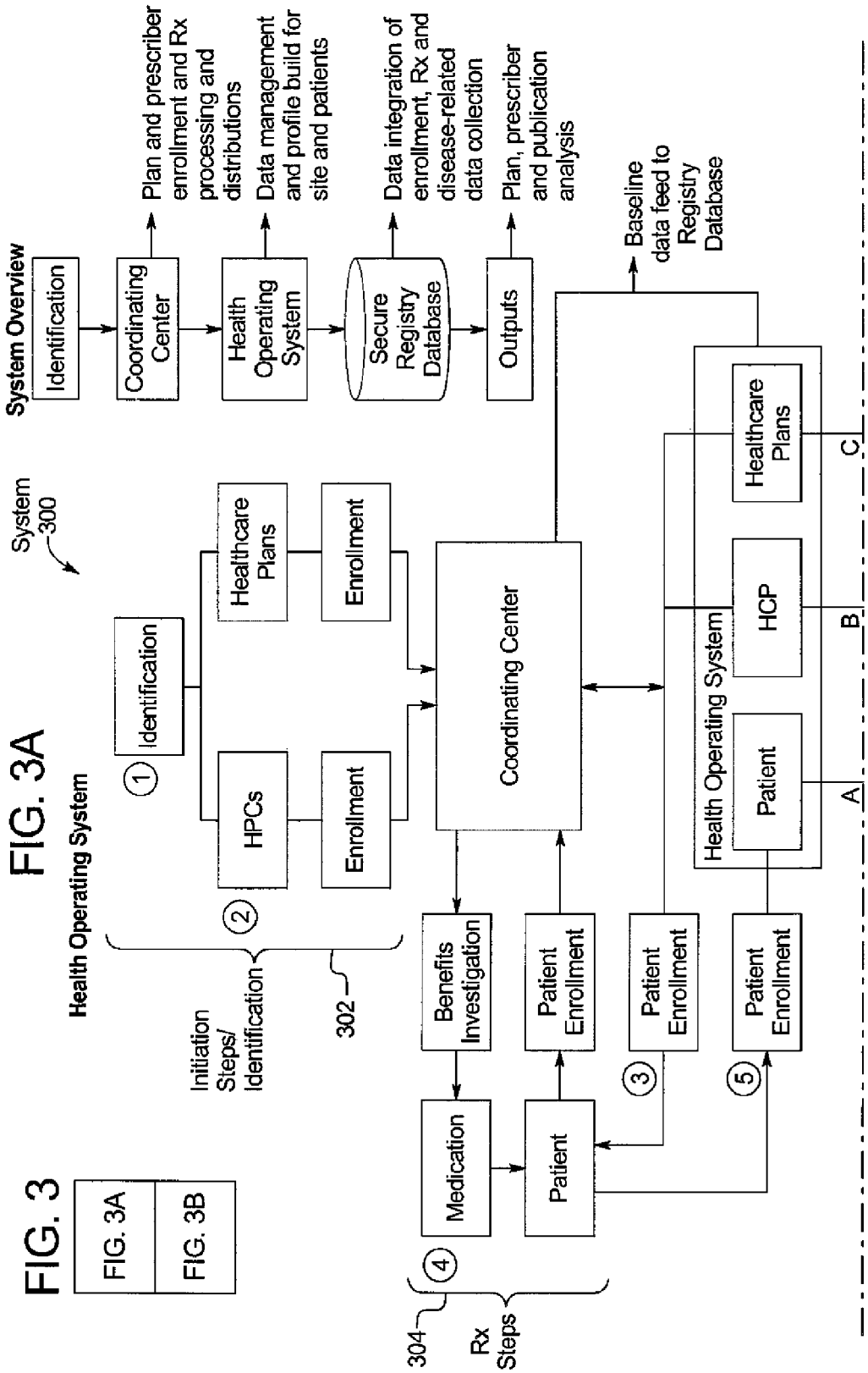
FIG. 3 is a block diagram showing one example of a system for obtaining and using outcome information associated with a prescription drug.
Figure 3B:
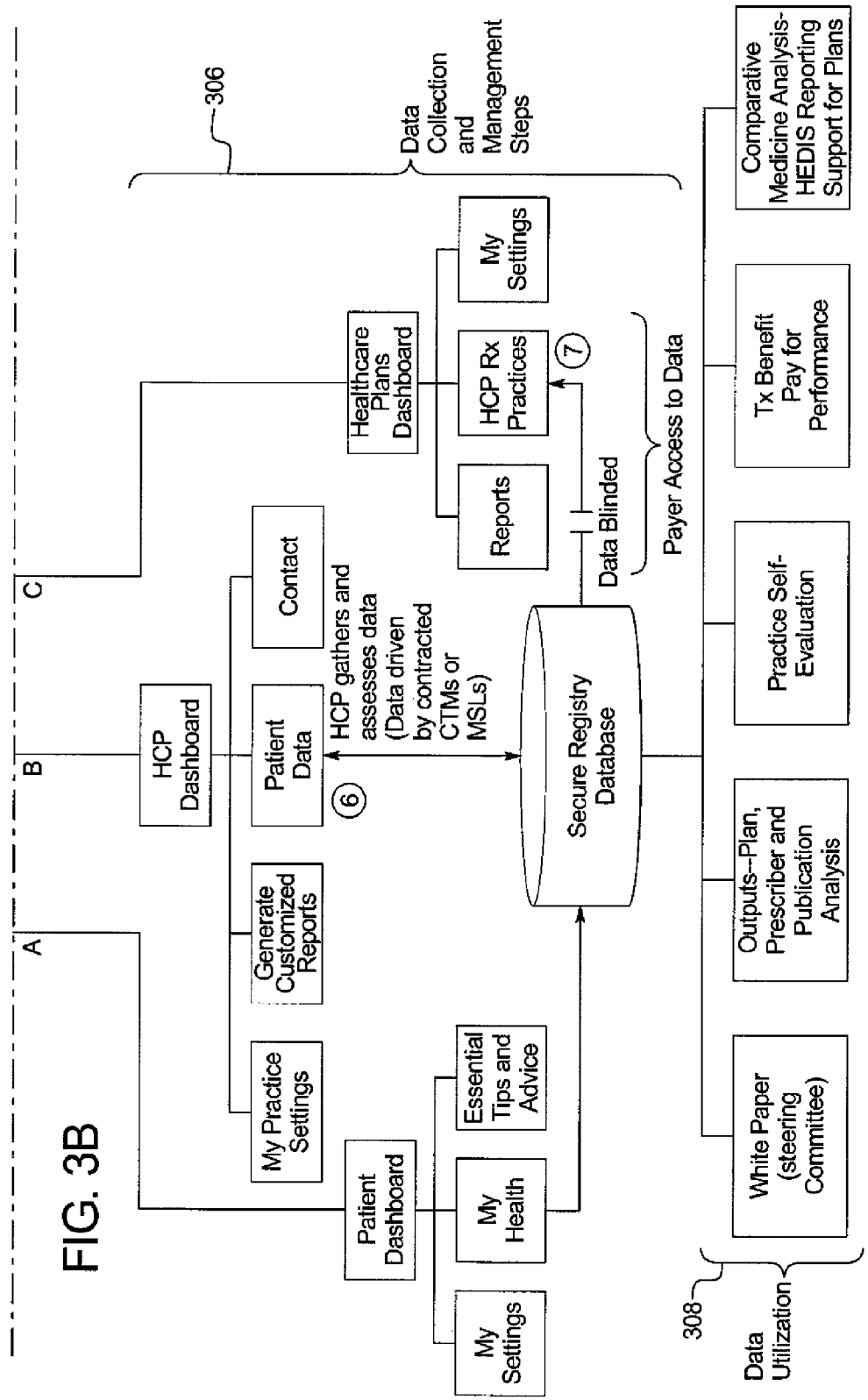

A block diagram showing one example of a system 300 for obtaining and using outcome information associated with a prescription drug (or medical device) is illustrated in FIG. 3. In this example, the system 300 includes initiation and identification blocks 302, RX blocks 304, data collection and management blocks 306, and data utilization blocks 308. Each of these sections of the system 300 are described briefly here and in more detail below with reference to FIGS. 4-18. Although the examples used through this specification refer to prescription drugs, a person of ordinary skill in the art will readily appreciate that some or all of these examples also apply to prescribed medical devices such as contact lenses, pace makers, or home hemodialysis machines.

The initiation and identification blocks 302 preferably include identification of health care providers/doctors (HCP) and payers/insurers that may be part of the system 300. Payers/insurers may be private and/or public payers/insurers and may include healthcare plans such as for example government plans (e.g., Medicare, Medicaid, VA, etc.), commercial carriers/insurance companies, managed care organizations, health maintenance organizations, preferred provider organizations, high risk insurance pools, special state programs and/or the patient (e.g., cash paying, self insured, uninsured, etc.). The system 300 may select (e.g., identify from a database those that meet certain criteria, exclude from a database those that do not meet certain criteria, receive selection input such as selection input manually) certain doctors and/or insurance companies for inclusion in the system 300 based on geography, volume, practice type(s) (e.g., specialty, size, etc), and/or patient populations. For example, practices with a high volume of patients with a certain chronic disease may be selected. Preferably, this portion 302 of the system 300 includes a streamlined registration process. For example, a doctor may complete an electronic enrollment form and submit the form via a website.

The RX blocks 304 preferably include patient enrollment, doctor prescriptions, and drug delivery. For example, a doctor prescribes a drug to a patient, and the patient is thereby registered in the system. For example, a doctor may complete an electronic prescription/patient registration form and submit the form via a website. Alternatively, the doctor may first register the patient in the system before prescribing the drug (e.g., prescription submission via a website). The drug is then provided (e.g., delivered) to the patient. For example, the system may ship (e.g., mail) the drug directly to the patient when requested and/or periodically from a central distribution facility. Alternatively, the system may provide instructions for shipment of the drug from a site (e.g., from a central distribution facility, from manufacturer, from a fulfillment partner, etc.) and/or for shipment of the drug to a site for patient pickup (e.g., doctor's office, on-site pharmacy of healthcare plan clinic). Alternatively, the system may provide instructions for release of the drug (e.g., to the patient directly or shipped) from inventory (e.g., existing inventory) at a pharmacy, such as a retail pharmacy, and/or any suitable fulfillment partner.

The data collection and management blocks 306 preferably include patient monitoring and data dashboards. Prior to initiating treatment with the drug (e.g., baseline) and/or after the patient has taken the drug (e.g., for some period of time), outcome information (e.g., outcome data) is collected. In order to collect the outcome information, the system may provide a data collection device or kit to the patient (e.g., by mail), instructions for shipment of a data collection device or kit to the patient, and/or instructions related to collection of outcome information (e.g., to the patient, to the patient's doctor). For example, if the drug was prescribed for hypertension, the patient may be provided with a blood pressure reading device in order to provide outcome information such as periodic blood pressure readings. Alternatively, or in addition, the patient may need to visit his/her doctor or alternatively a laboratory (e.g., diagnostic laboratory) to collect certain outcome information.

The outcome information may be viewed by the patient, the doctor, and/or the healthcare plan (e.g., in aggregate) via a software dashboard. For example, a patient may log in to a website and view a graph of his/her blood pressure readings. In another example, a doctor may query the system to see what percentage of his/her male patients over thirty years old have a reduced blood pressure after six months on a particular drug prescribed for hypertension. In yet another example, a health care plan and/or a managed care organization may request a report comparing the effectiveness of two different drugs. In another example, a doctor and/or a health care plan and/or a managed care organization may check for compliance (e.g., Does it appear that the patient is taking the drug according to the prescribed dosage and frequency and/or is the prescription being refilled?)

The data utilization blocks 308 include publication of aggregate information (e.g., outcome information), analysis of outcome information, and utilization of the outcome information to achieve one or more results (e.g., drive medical decisions). For example, the outcome information may be used to influence compliance and/or adherence of a prescription drug based. In another example, the outcome information may be used to select a different medical prescription. In another example, the outcome information may be used to market a prescription drug. For example, the outcome information may be used to market a prescription drug by showing a doctor outcome information associated with that drug and/or a competitive drug. In yet another example, the outcome information may be used to develop a new drug.

Figure 4:
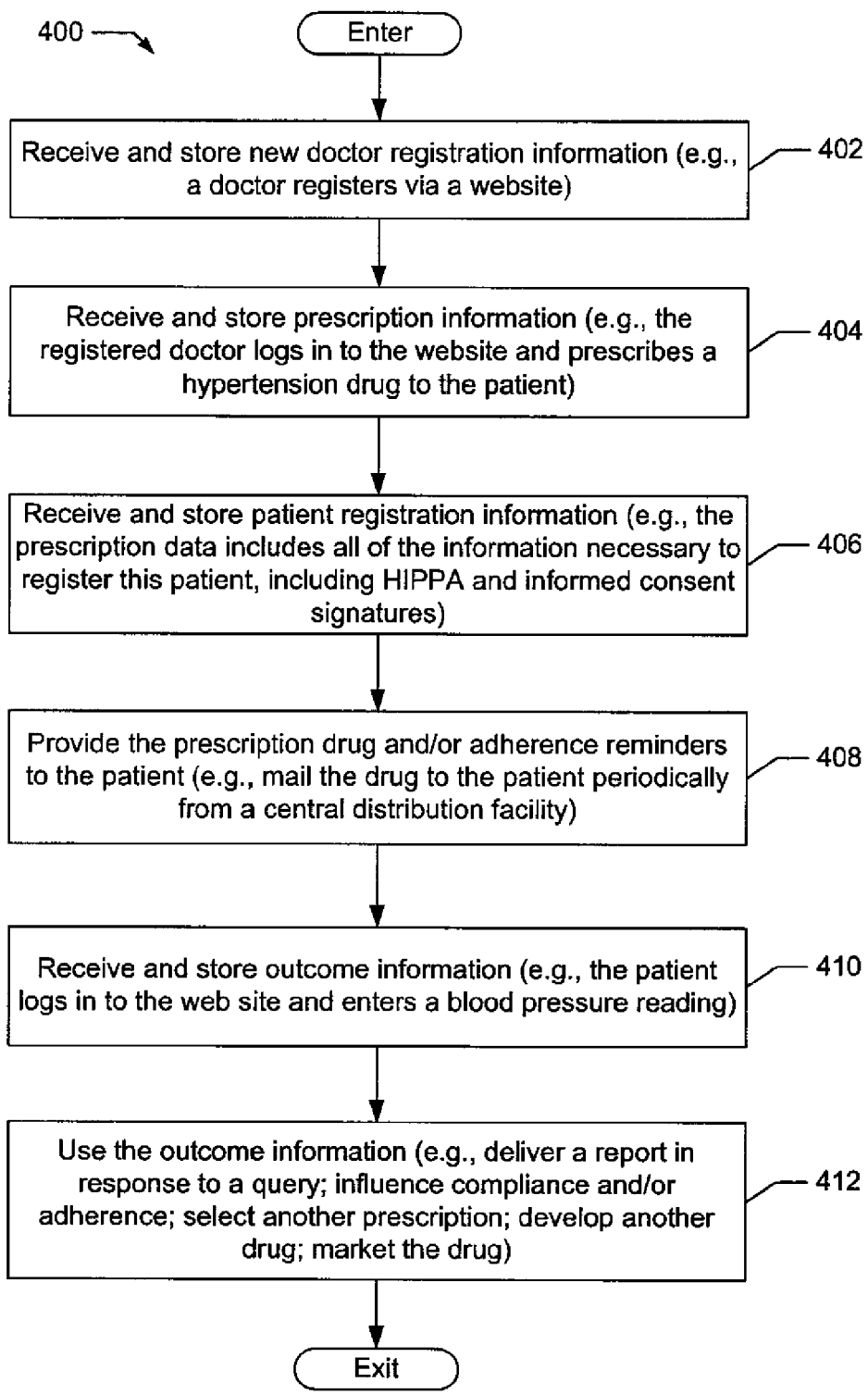
FIG. 4 is a flowchart showing one example of a process for obtaining and using outcome information associated with a prescription drug.

A flowchart of an example process 400 for obtaining and using outcome information associated with a prescription drug (or medical device) is presented in FIG. 4. Preferably, the process 400 is embodied in one or more software programs, which are stored in one or more memories and executed by one or more processors. Although the process 400 is described with reference to the flowchart illustrated in FIG. 4, it will be appreciated that many other methods of performing the acts associated with process 400 may be used. For example, the order of many of the steps may be changed, some of the steps described may be optional, and additional steps may be included.

In general, the process 400 facilitates the registration of doctors and patients in a system (e.g., central prescription distribution system). Once registered, the system may permit and/or facilitate doctors in the system to prescribe drugs to patients, which in turn registers the patients in the system. Alternatively, once registered, the system may permit and/or facilitate doctors in the system to prescribe drugs to patients and register patients in the system during the same submission, or to prescribe drugs to patients already registered in the system (e.g., patients registered previously by the same doctor or a different doctor). Prescribed drugs are provided to the patient, preferably by shipment from one or more distribution hubs directly to the patient. Outcome information associated with prescription drugs provided to patients is then collected (e.g., from the patients) and used in a variety of ways.

More specifically, a system using the example process 400 begins by receiving and storing new doctor registration information in a centrally accessible system (block 402). For example, the doctor registration information may be from a doctor completing an electronic registration form and submitting the form to the system via a website or email. Alternatively, the information may be from a doctor completing a paper form and sending the form to the system via facsimile, regular mail, and/or a scanned e-mail attachment. In yet another example, the information may be from a doctor registering via a live telephone operator and/or an automated touch tone system. Preferably, doctor registration in the system (e.g., the submission and storage of the doctor registration information) is not mandated by a government agency such as a government approval agency (e.g., the Food and Drug Administration). In some embodiments, the majority of doctors or substantially every doctor allowed to prescribe the prescription drug is registered in the system (e.g., greater than or equal to some percentage such as 50%, 60%, 70%, 80%, 90%, OR 100%).

An example of a doctor registration form is illustrated in FIG. 17. As shown, doctor registration information preferably includes some or all of the doctor's name, address, telephone number, fax number, email address, state license number, ME number, DEA number, MPI number, practice area, specialties, etc. In addition, the doctor registration information preferably includes a prescriber agreement and the doctor's signature on that agreement. For example, the doctor may agree to adhere to one or more requirements or regulations of a government agency (e.g., requirements of the Health Insurance Portability and Accountability Act (HIPAA)), to obtain appropriate patient consent (e.g., informed consent), to educate the patient about the side effects of the drug and/or to collect certain outcome information (e.g., MRI data). Some or all of the doctor registration may be selected from a menu and/or manually entered or edited.

Returning to the flowchart in FIG. 4, a system using the process 400 receives and stores prescription information (block 404). For example, prescription information may be from a doctor completing an electronic prescription/patient registration form and submitting the form to the system via a website or email. Alternatively, the information may be from a doctor completing a paper form and sending the form to the system via facsimile, regular mail, and/or e-mail attachment. In yet another example, the information may be from a doctor prescribing a drug via a live telephone operator and/or an automated touch tone system.

An example of a prescription/patient registration form is illustrated in FIG. 18. As shown, prescription information preferably includes doctor data, patient data, and drug data. Doctor data preferably includes some or all of the doctor registration information, such as the doctor's prescribing number. Patient data preferably includes the patient's name, address, phone number, insurance information, etc. Drug data preferably includes a drug identifier, a dose, and administration instructions.

Figures 9, 10:
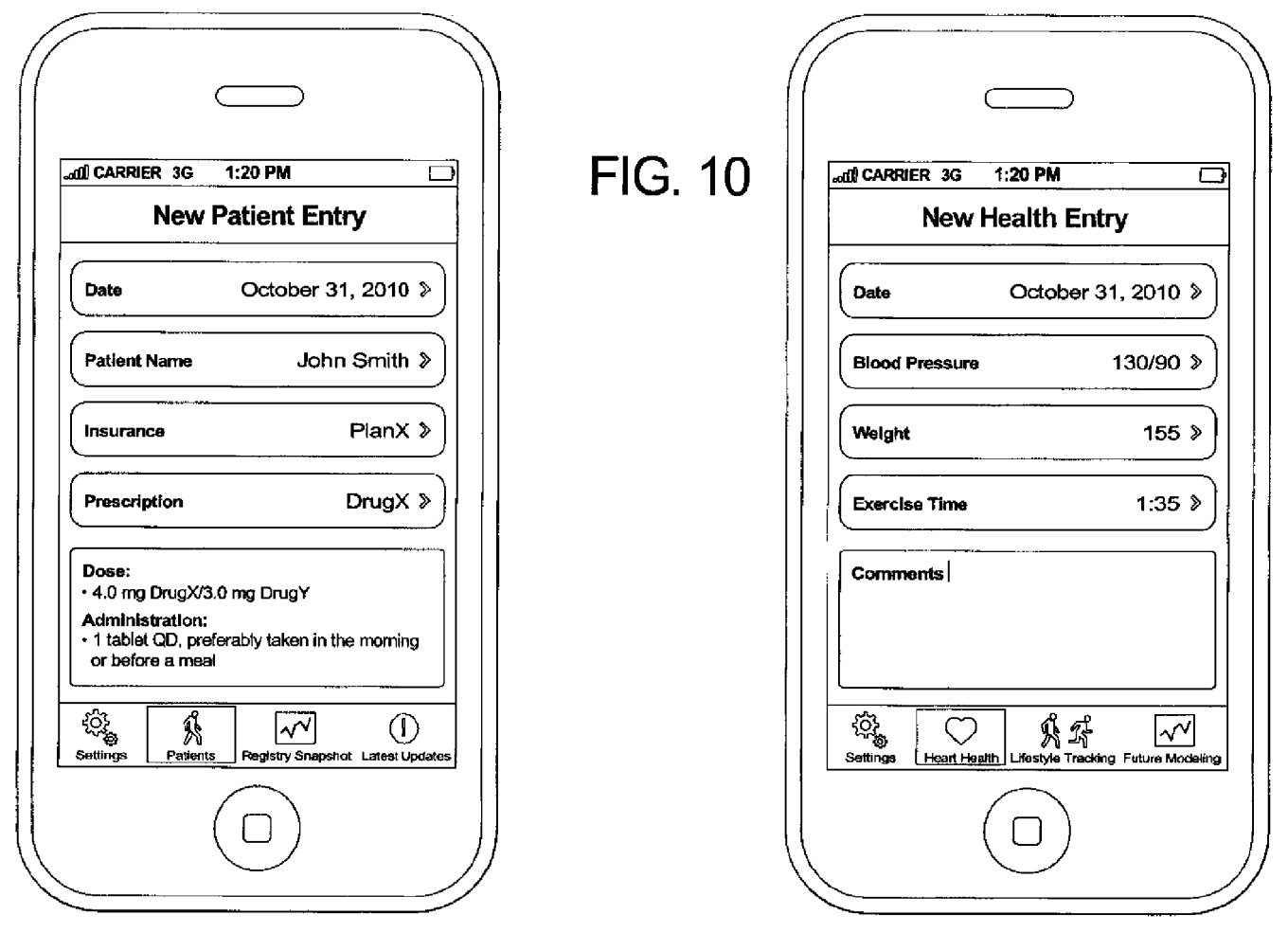

A screen shot of an example prescription application is illustrated in FIG. 9. In this example, the doctor prescribes DrugX to John Smith. Preferably, the system assists the doctor's selections, and some or all of the prescription information may be selected from one or more menus. For example, once a drug is selected, the system preferably limits the dosage choices and/or administration instructions (e.g., consumption frequency) to the dosages and/or administration instructions actually available for that drug. In this example, different patients associated with the registered and/or logged in doctor may be selected from a menu. Similarly, an insurance company may be selected or may be automatically populated from a previous selection for the current patient. Other information associated with the patient may also be entered such as the patient's age, weight, sex, medical history, etc. The patient information is then preferably transmitted over a network to the central system.

Returning to the flowchart in FIG. 4, a system using the process 400 also receives and stores patient registration information (block 406). Patient information may be received directly from the doctor. For example, patient information may be included in the transmitted prescription information as described above with reference to FIG. 18. Accordingly, the patient information may be stored when the prescription information is received from the doctor, and the patient need not be pre-registered to use the system. Alternatively, patient information may be received indirectly from the doctor. For example, patient information may be received from a doctor's staff, a hospital, a health care plan (e.g., a health care plan the doctor is affiliated with), a managed care organization (e.g., HMO and/or a managed care organization the doctor is affiliated with), a clinic, an independent third party, etc. Alternatively, the patient information may be in the system from a previous registration (e.g., pre-registered), such as for example patient information received from the same doctor (e.g., for a previous prescription) or a different doctor (e.g., for unrelated treatment). In any of these embodiments, the patient information may be received in the form of electronic medical records.

Preferably, the patient registration information includes HIPPA and informed consent signatures. However, the submission and storage of other patient registration information is not mandated by a government agency such as the FDA. In some embodiments, the majority of patients or substantially every patient allowed to take the prescription drug is registered in the system (e.g., greater than or equal to some percentage such as 50%, 60%, 70%, 80%, 90%, OR 100%).

Like doctors and patients, private and/or public payers/insurers (e.g., health care plans and/or managed care organizations) may also register with the system. For example, health care plan registration information may be from a representative of a health care plan completing an electronic registration form and submitting the form to the system via a website or email. Alternatively, the information may be from a health care plan representative completing a paper form and sending the form to the system via facsimile, regular mail, and/or a scanned e-mail attachment. In yet another example, the information may be from a health care plan representative registering via a live telephone operator and/or an automated touch tone system. Preferably, health care plan registration in the system and/or a managed care organization registration in the system (e.g., the submission and storage of the health care plan registration information) is not mandated by a government agency such as the Food and Drug Administration (FDA). In some embodiments, the majority of health care plans and/or a managed care organizations, or substantially every health care plan and/or a managed care organization allowed to use the system is registered in the system (e.g., greater than or equal to some percentage such as 50%, 60%, 70%, 80%, 90%, OR 100%)

Figure 5:
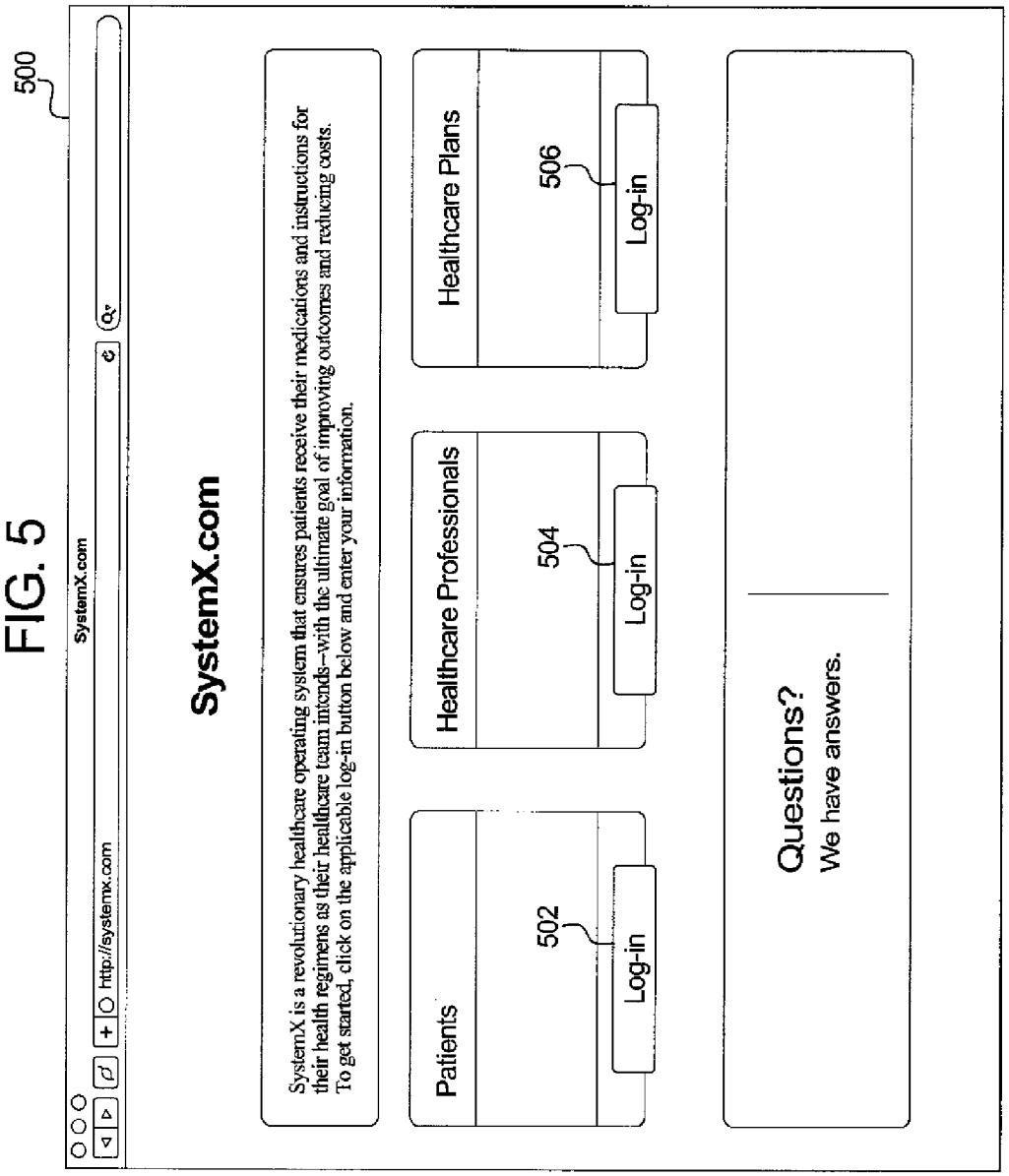
FIG. 5 is a screen shot of an example of a login page.

The system may permit and/or facilitate individuals (e.g., patients and/or doctors) or organizations (e.g., medical offices, managed care organizations and/or health care plans) that are registered with the system to access the system to perform certain tasks and review certain data. Preferably, individuals' and organizations' access to the system is by logging in via a web page or web based application. A screen shot of an example login page 500 is illustrated in FIG. 5. In this example, patients', healthcare professionals', and healthcare plan providers' access may be by logging in to the system using log in buttons 502, 504, and 506 respectively. Access to the system by individuals and organizations that are registered with the system may also be in any other suitable manner. For example, individuals' or organizations' access to the system may be via facsimile, e-mail, regular mail, and/or touch tone telephone.

The system may permit and/or facilitate patients' access to the system to request prescribed drugs. For example, if a patient's prescription includes one or more refills, the system may permit a patient to log in to the system to request a refill. In such an instance, the system may determine that the request is early and deny or delay the refill. For example, if each fulfillment of the prescription includes a one month supply, and the patient request comes only two weeks after the last fulfillment, the system may determine that the request is too early and deny or delay the refill. In addition, the system may notify the prescribing doctor (e.g., prescriber) of the fulfillment of a prescription and/or any other event, such as denying or delaying a refill. Notifications to patients and doctors may be performed in any suitable manner. For example, the system may send the doctor an email, generate an automated phone message, or simply store the data for later retrieval by the doctor.

Conversely, the system may determine that the request is late and warn the patient and/or the prescriber about compliance. For example, if each fulfillment of the prescription includes a one month supply, and the patient request comes six weeks after the last fulfillment, the system may determine that the request is late and warn the patient and/or notify the prescriber of this event. For example, the system may notify the patient about medical risks associated with not adhering to the prescription and notify the doctor that the patient is not adhering to the prescription. Notifications to patients and doctors may be performed in any suitable manner. For example, the system may send patients and/or doctors an email message, generate an automated phone message, or store the messages for later retrieval by the patient sand/or doctors.

Alternatively, an election may be made (e.g., by the patient, by the doctor) to have the system automatically send each refill of a prescription at the correct time based on the amount of the drug previously provided to the patient and the associated administration instructions. For example, if each fulfillment of the prescription includes a one month supply, the system may automatically mail refills or provide instructions to mail refills to the patient's home address every thirty days starting with the initial fulfillment. In this manner, the patient is more likely to fill his/her entire prescription (e.g., all prescribed refills) than in a typical retail environment where a physical visit to a pharmacy may be required. In addition, the patient is more likely to adhere to the prescription, because of the automatic fulfillment.

The system may permit and/or facilitate patients' access to the system to review their own outcome information. For example, if the drug is prescribed for hypertension, the patient may be required to periodically take his/her own blood pressure and enter that data in to the system (as described in detail below). In this example, the patient may be allowed to access the system and review those blood pressure readings. For example, the system may permit the patient to log in to a website and view a graph of his/her blood pressure readings. In another example, the system may read the patient's outcome information over the telephone or send an email message that includes the patient's outcome information.

Returning to the flowchart in FIG. 4, a system using the process 400 also provides the prescription drug and/or a reminder to the patient (block 408). For example, the system may mail or provide instructions to mail the drug directly to the patient when requested and/or periodically. Preferably, the prescription drug is not available at retail locations (e.g., no retail locations, limited number of retail locations) via distribution from a manufacturer of the prescription drug and/or a wholesale distributor of prescription drugs.

Preferably, the drug is mailed from a central distribution facility. However, the drug may be mailed from a manufacturer upon request from (e.g., instructions provided by) the system. As described above, the system may permit and/or facilitate patients to access the system (e.g., via a website) and request refills. Alternatively, the system may permit and/or facilitate patients to request automatic refills (e.g., every thirty days) per his/her doctor's prescription.

Alternatively, the drug may be sent to the doctor's office for pick up by the patient. In this manner, the doctor may perform certain follow up education (e.g., regarding diet, exercise, side effects, complications, etc.) for the patient and/or collect certain outcome information (e.g., an MRI). Preferably, the doctor does not keep an inventory of the drug. Instead, the doctor only receives the drug at or about the time the drug is needed for a particular patient.

In yet another alternative, one or more of the drugs provided by the system may be kept in an inventory of a closed health care plan (e.g., health care program, health care network, managed care organization), such as a veteran's affairs plan or health maintenance organization (HMO). In some instances, the closed plan may mail the drug to the patient. In other instances, the patient visits an onsite pharmacy of a clinic associated with the closed plan to pick up the drug. In any case, permission or instructions to distribute the drug to the patient comes from (e.g., originates from) the system (e.g., central distribution system) based on a registered doctor's prescription for that patient.

In addition, the system may send the patient one or more reminders to refill a prescription. For example, the system may send the patient an email or an automated telephone reminder around the time the patient should be refilling their prescription. In some embodiments, the reminder is sent prior to the normal renewal time prompting the patient to request their refill. In some embodiments, the reminder is sent after the normal renewal time prompting the patient to request their refill and informing the patient about the risks of not adhering to their prescription.

Once the patient has been taking the prescription drug for a period of time, the system receives from certain outcome information (e.g., from the patient and/or the doctor), which is stored in the central system (block 410). The type of outcome information collected is preferably predetermined by the prescribing doctor and/or a steering committee (e.g., a group of doctors that specialize in a certain field of medicine) based on the indicated medical condition associated with the prescription drug. For example, if the drug was prescribed for hypertension, the patient may be provided with a blood pressure reading device in order to provide periodic blood pressure data. If the drug was prescribed for a neurological condition, the patient may be required to periodically visit his doctor for an MRI. Outcome information may be received directly (e.g., as in the examples above) or indirectly from the patient and/or the doctor. For example, outcome information may be received from a doctor's staff, a hospital, a health care plan (e.g., a health care plan the doctor is affiliated with), a managed care organization (e.g., HMO and/or a managed care organization the doctor is affiliated with), a clinic, a third party (e.g., an independent third party including, for example a diagnostic or testing lab), etc. In some instances, the system may permit and/or facilitate a user of the system to encourage and/or require certain types of outcome information to be collected. For example, a health plan and/or a managed care organization may query the outcome information and determine that doctors that collect certain outcome information (e.g., weekly body weight) often show better results (e.g., less heart attacks) for a certain prescription drug than doctors that do not collect that outcome information.

Preferably, this information is periodically collected or received by (e.g., submitted to) the system, such as for example, daily, weekly and/or monthly. For example, a person may periodically visit the participating doctor's offices and/or the outcome information may be electronically transited to the system. Preferably, the submission and storing of the outcome information is not mandated by a government agency such as the FDA.

A screen shot of an example outcome information collection application is illustrated in FIG. 10. In this example, information (e.g., data) for blood pressure, weight and exercise time may be selected from a menu and/or manually entered. Outcome information collection may also be performed via doctor and/or patient dashboards as described in detail below.

Returning to the flowchart in FIG. 4, a system using the process 400 may use the outcome information (block 412). For example, the outcome information may be used to generate and/or deliver a report in response to a query via a software dashboard. A query may come from a doctor, a payer, a patient, a government agency, a health care plan, and/or a managed care organization.

A screen shot of an example patient dashboard 600 is illustrated in FIG. 6. In this example, the patient dashboard 600 includes a data submission section 602 and a data display section 604. The data submission section 602 may be used to enter patient information and/or outcome information. In this example, patient information includes the patient's weight, exercise time, and diet. It will be appreciated that any patient information, such as name, age, sex, ethnicity, other medications, other comorbidities, etc. may be entered via the patient dashboard 600. In this example, outcome information includes the patient's blood pressure. It will be appreciated that any outcome information, such as weight, events, pain descriptions etc. may be entered via the patient dashboard 600. Depending on the drug and/or indicated condition, certain data may be considered patient information and/or outcome information. For example, if the drug is prescribed for hypertension, weight may be considered patient information. If the drug is prescribed for weight loss, weight may be considered outcome information.

The data display section 604 may be used to display patient information and/or outcome information. In this example, patient information includes the patient's weight, exercise time, drug and diet. It will be appreciated that any patient information, such as name, age, sex, ethnicity, etc. may be displayed via the patient dashboard 600. In this example, outcome information includes the patient's blood pressure. It will be appreciated that any outcome information, such as weight, events, pain descriptions etc. maybe displayed via the patient dashboard 600. Again, depending on the drug and/or indicated condition, certain data may be considered patient information and/or outcome information (e.g., weight).

Figure 7:
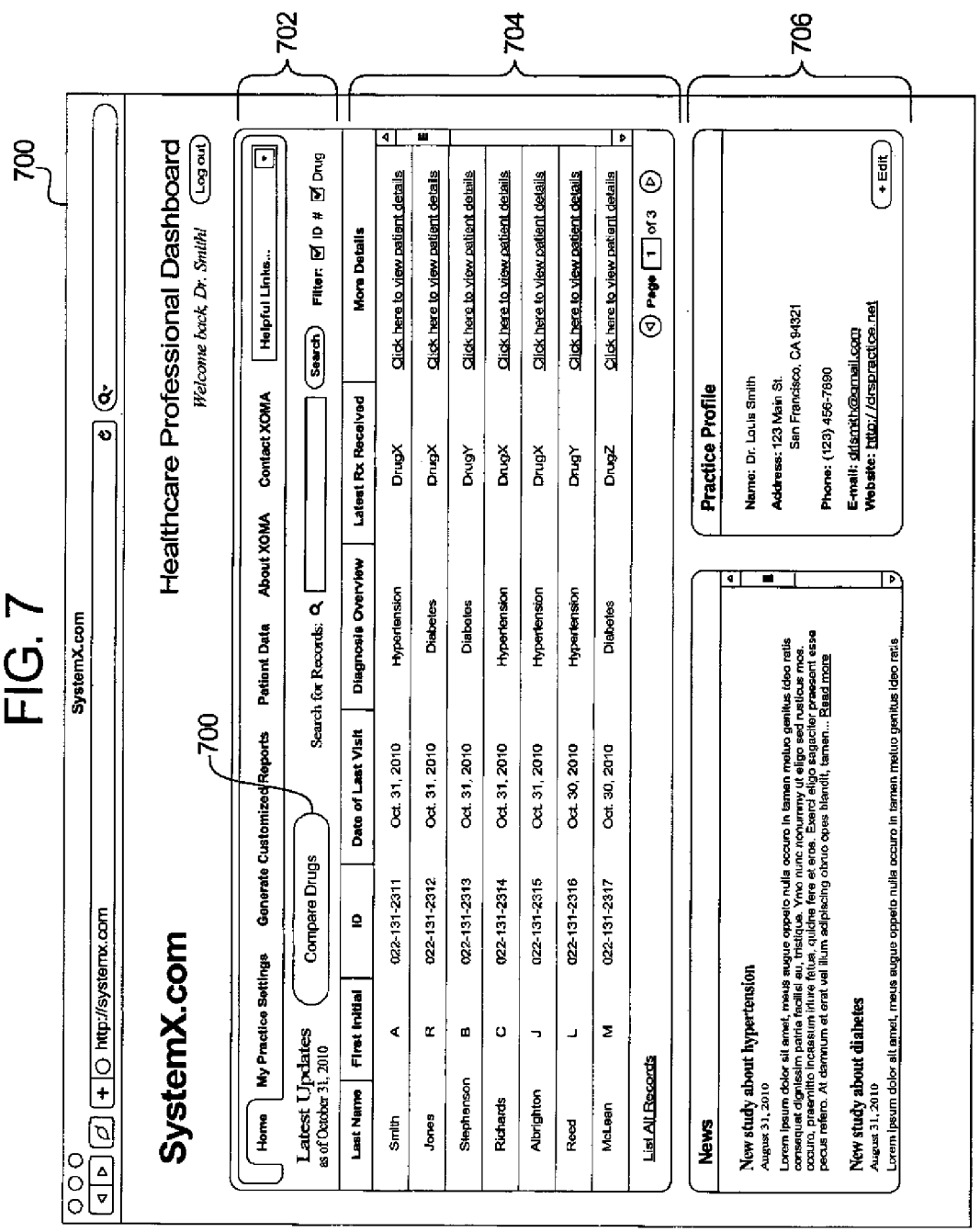
FIG. 7 is a screen shot of an example of a healthcare professional dashboard.

A screen shot of an example health care provider dashboard 700 is illustrated in FIG. 7. In this example, the health care provider dashboard 700 includes a query section 702, a data display section 704, and a miscellaneous section 706. The query section 702 may be used to find a patient or run reports using aggregated outcome information from multiple patients. For example, a doctor may want to see what percentage of male patients over 30 have reduced their blood pressure after six months on a particular drug prescribed for hypertension.

In this example, the query section 702 includes a compare feature 700. The compare feature 700 allows a doctor to compare the effectiveness of two different drugs. For example, a doctor may want to compare the effectiveness of Drug X to the effectiveness of Drug Y.

An example of a drug comparison chart 800 is illustrated in FIG. 8. In this example, five patients taking Drug X are compared to five patients taking Drug Y. The example drug comparison chart 800 includes patient information and outcome information. The patient information includes a patient identifier (e.g., a patient number), the drug the patient is taking (e.g., drug X or drug Y), and the number of days the patient has been taking the drug (e.g., 30 days). If the user is a doctor, the patient identifier may be unique (e.g., name, social security number, etc.), otherwise the patient identifier is preferably generic (e.g., 1, 2, 3, etc.). The outcome information includes the patient's overall blood pressure trend (e.g., decreased), and any events associated with the patient's diagnosed condition (e.g., cardiovascular event, stroke).

Returning to the health care provider dashboard 700 illustrated in FIG. 7, the example data display section 704 includes a plurality of different patients taking a plurality of different drugs. In this example, each patient is identified by name (e.g., Harris) and identification number (e.g., 022-131-2311). Patients with the same diagnoses may be taking the same or different drugs. For example, patients Kitteredge, Hampts, and Rondelle are all diagnosed with hypertension. Kitteredge and Hampts are both taking Drug X. However, Rondelle is taking Drug Y. Patients with different diagnoses may also be taking the same or different drugs. For example, patient Harris is diagnosed with hypertension and patient LaRoux is diagnosed with diabetes. However, both Harris and LaRoux are taking Drug X.

The miscellaneous section 706 of the health care provider dashboard 700 includes other information such as news and doctor information. In one embodiment, the news is automatically correlated to the diagnoses being displayed. For example, if the data display section 704 includes patients diagnosed with hypertension, the miscellaneous section 706 may display news about hypertension, such as new hypertension studies, hypertension drugs, tips to decrease cardiovascular risk, etc.

Returning to the flowchart in FIG. 4, a system using the process 400 may use the outcome information for purposes other than reporting (block 412). For example, the outcome information may also be used to influence compliance and/or adherence. For example, the system may notify the patient about medical risks associated with not adhering to the prescription and/or notify the doctor that the patient is not adhering to the prescription. Evidence of this influence may be numerical. For example, a patient or group of patients may refill prescriptions closer to the prescribed schedule than that patient or group had previously refilled prescriptions. In another example, a group of patients using the system may have a higher percentage of initial fills and/or refills than another group of patients that are not using the system. Similarly, a group of patients taking one or more drugs for a certain indication (e.g., hypertension) using the system may have a higher percentage of initial fills and/or refills than a similar group of patients taking one or more drugs for the same indication (e.g., hypertension) that are not using the system.

Based on comparative reports, the outcome information may be used to select another prescription for a patient. The new prescription may be for a different dose of the same drug, an alternate drug, an additional drug, a different consumption frequency, a different time of day, etc. Similarly, outcome information may also be used to develop another drug. The new drug may have the same and/or different active ingredients as drugs that are studied using the system. The outcome information may also be used to market the drug and/or the system itself. For example, doctors may be receptive to participating in a system that offers evidence-based data and/or increased patient compliance or adherence. In addition, doctors may find comparisons of drugs convincing.

Figure 11:
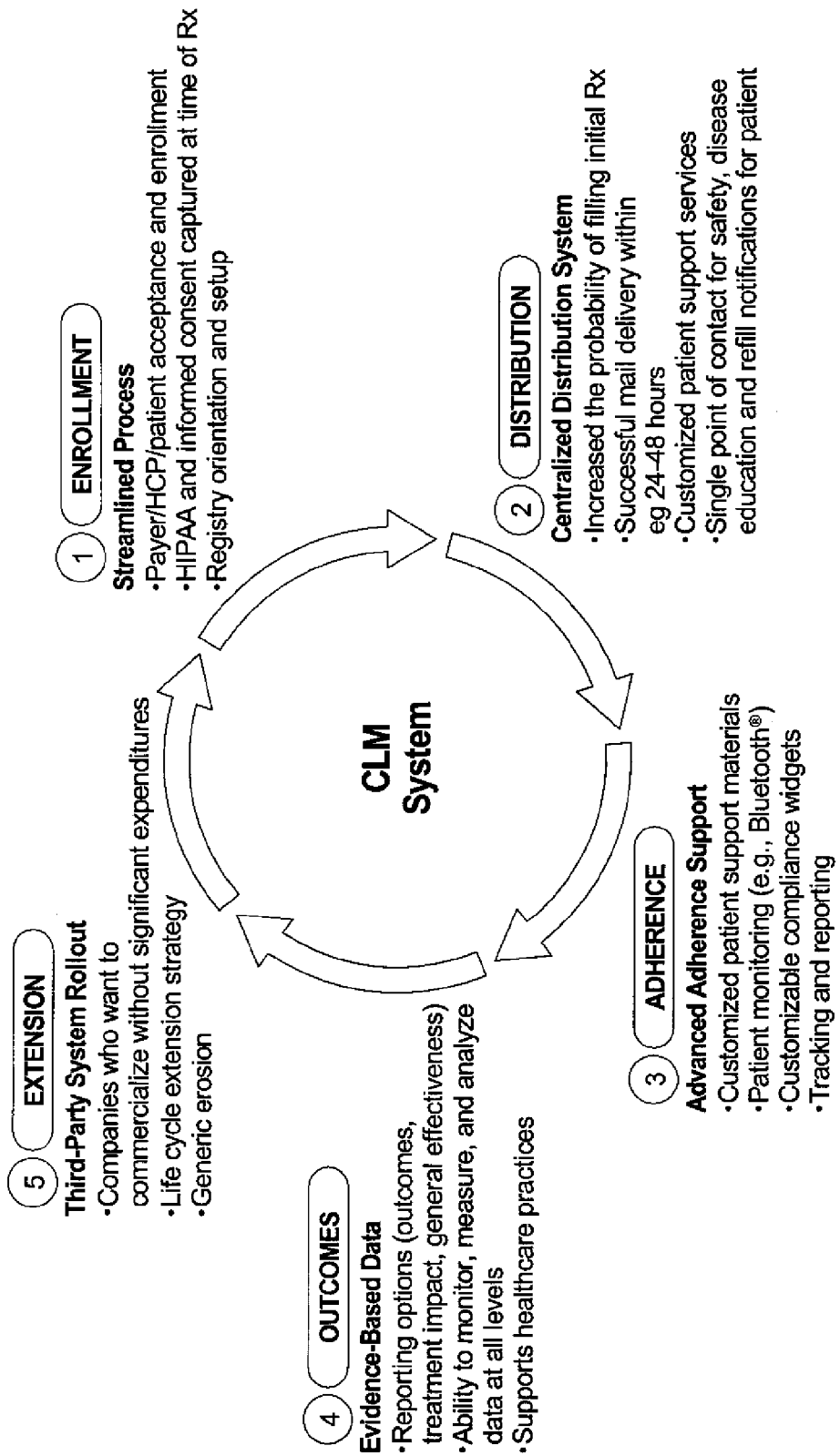
FIG. 11 is a flow diagram showing another example of a process for obtaining and using outcome information associated with a prescription drug.

A flow diagram showing another example of a process for obtaining and using outcome information associated with a prescription drug is illustrated in FIG. 11. In this example, the system includes an enrollment phase, a distribution phase, an adherence phase, an outcomes phase, and an extension phase.

The enrollment phase includes a streamlined process for acceptance and enrollment, capture of HIPPA and informed consent, and registry orientation and setup. As described above with reference to blocks 402-404 of FIG. 4, the acceptance and enrollment of payers, health care providers, and patients preferably includes a web based enrollment process, but may include other suitable enrollment processes, such as paper forms. Preferably, the capture of HIPPA and informed consent is accomplished by capturing the patient's signature at the time the prescription is written. For example, the doctor may have the patient sign the necessary forms and the system receives such forms uploaded or attached at the time the doctor submits the prescription. Alternatively, the system may receive from the doctor's submission a statement that he/she has obtained the patient's HIPPA and informed consent, which may be maintained with the doctor's files. Registry orientation and setup is preferably is performed via the software dashboards described above.

The distribution phase may utilize a central distribution system that increases the probability of filing initial prescriptions, delivers the prescribed drug within a short period of time (e.g., 24-48 hours), customizes patient support services, and acts as a single point of contact for safety, disease education, and refill notification. As described above with reference to block 408 of FIG. 4, the initial prescriptions are automatically provided (e.g., shipped) directly to the patient in response to a doctor's prescription with no retail middleman, therefore patients do not have to travel to a pharmacy or submit for alternative prescription fulfillment (e.g., mail order), prices may be reduced, and/or fulfillment percentages increase. Additional benefits may include that patients may be notified of upcoming refills, missed refills, or receive automatic refills.

As described above with reference to blocks 408-410 of FIG. 4, the adherence phase includes customized patient support materials, patient monitoring, compliance widgets, tracking, and reporting. For example, patients may receive an email message, automated phone message, or a message via their dashboard that describes the methods and reasons for adherence to their specific drug. In addition, email, phone and/or dashboard reminders may help the patient adhere to the prescription. As described above, outcome information is collected during this phase. For example, if the drug was prescribed to reduce cholesterol, the patient may be provided with a home cholesterol measurement kit. Alternatively, or in addition, the patient may need to visit his/her doctor to collect certain outcome information (e.g., x-ray).

As described above with reference to block 412 of FIG. 4, the outcomes phase may include evidence-based data for multiple different parties via various reports, treatment impacts, drug effectiveness data, and analysis. For example, the system may permit and/or facilitate a patient to log in to a website and view a graph of his/her body weight over time. The system may permit and/or facilitate a doctor to query the system to see what percentage of his/her female patients under forty years old have a reduced blood pressure after a year on a particular drug prescribed for hypertension. The system may permit and/or facilitate a health care plan and/or a managed care organization to request a report comparing the effectiveness of two different drugs.

The extension phase may include third-party use of the system. For example, certain other companies may want to commercialize one or more prescription drugs using the described system.

Figure 12:
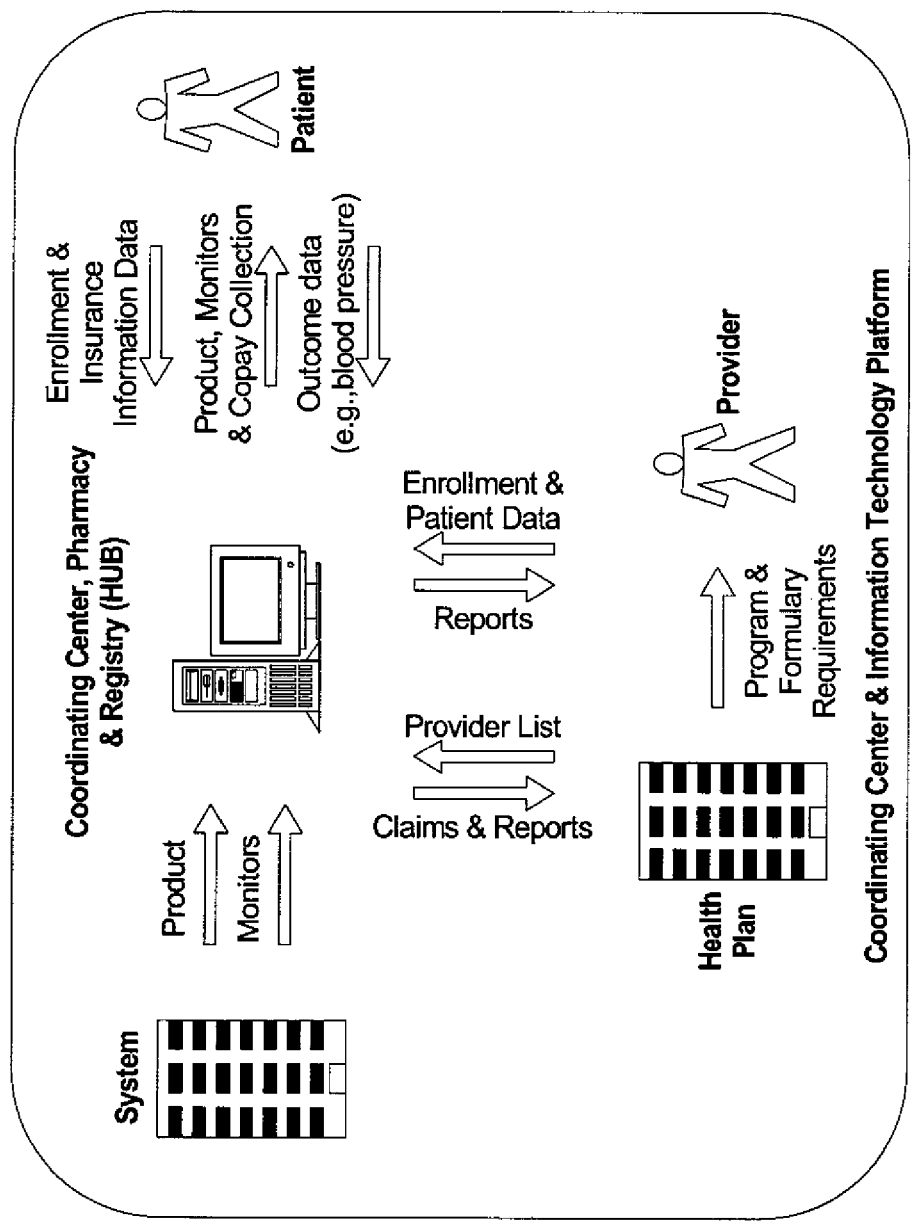
FIG. 12 is a block diagram showing another example of a system for obtaining and using outcome information associated with a prescription drug.

A block diagram showing another example of a system for obtaining and using outcome information associated with a prescription drug is illustrated in FIG. 12. In this example, a central hub is responsible for data collection, shipping drugs (e.g., providing instructions to a third party to ship drugs) and outcome collection devices, verifying patient benefit information, adjudication of insurance claims and/or reporting. The system, which may include the hub, is responsible for providing (e.g., shipping, providing instructions to ship) drugs and outcome collection devices to the patients. The system is also responsible for receiving certain information, such as for example the information from the following individuals and/or organizations. Providers are responsible for enrolling in the program, prescribing to patients, and providing patient data. Health plans, managed care organizations, and/or drug manufactures are responsible for providing a comprehensive provider list to the system (e.g., central registry) and informing providers of program requirements. The patient, the patient's doctor and/or a healthcare plan are preferably responsible for enrolling the patient in the program and providing outcome information at required intervals.

Figure 13:
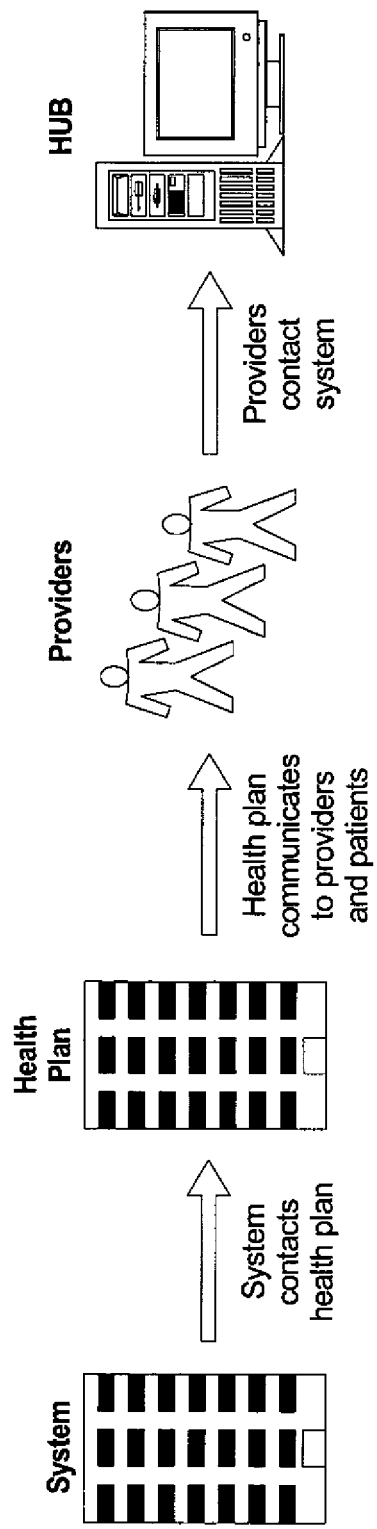
FIG. 13 is a flow diagram showing an example of a process for payer contracting.

A flow diagram showing an example of a process for payer contracting is illustrated in FIG. 13. In this example, the system contacts one or more health plans and/or a managed care organizations to participate in the program and negotiates discounted pricing on products to ensure preferred formulary status with the health plan and/or a managed care organization. The system permits and/or facilitates the health plan and/or a managed care organization to then communicate to a network of healthcare providers and/or patients informing them of the program requirements and the preferred formulary status. The system permits and/or facilitates the healthcare providers to then contact the system for education and enrollment information in order to prescribe drugs to patients.

Figure 14:
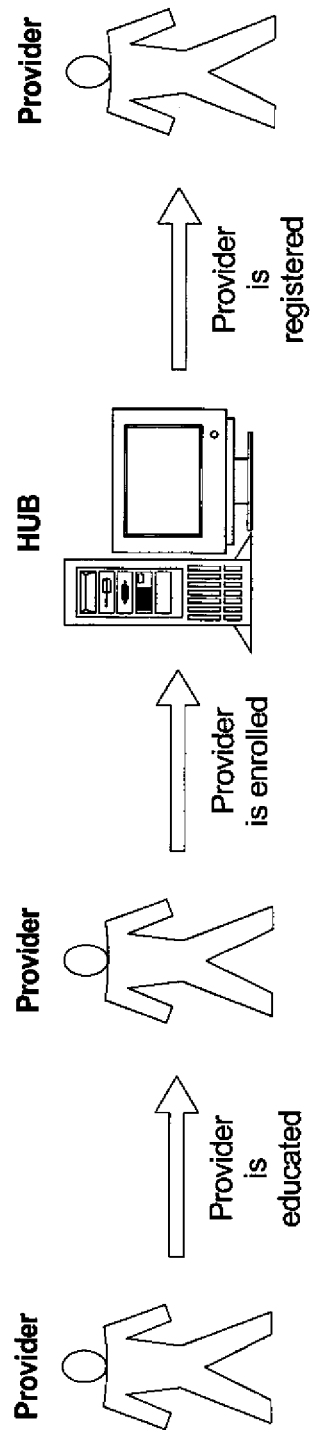
FIG. 14 is a flow diagram showing an example of a process for healthcare provider enrollment.

A flow diagram showing an example of a process for healthcare provider enrollment is illustrated in FIG. 14. In this example, a healthcare provider is educated on one or more prescription drugs and the program. The system permits and/ or facilitates the healthcare provider to then complete a doctor enrollment form, agreement to participate in the program, and submission of the doctor enrollment form to the system (e.g., via web, fax, or mail). The system then verifies that the submitted information is complete (e.g., includes information in the state license # field) and accurate (e.g., the state license # actually belongs to this doctor). If the information is complete and accurate, the healthcare provider is registered in the system database. Subsequently, the healthcare provider is authorized to write prescriptions for patients, which in turn may enroll those patients in the system, if they are not already registered.

Figure 15:
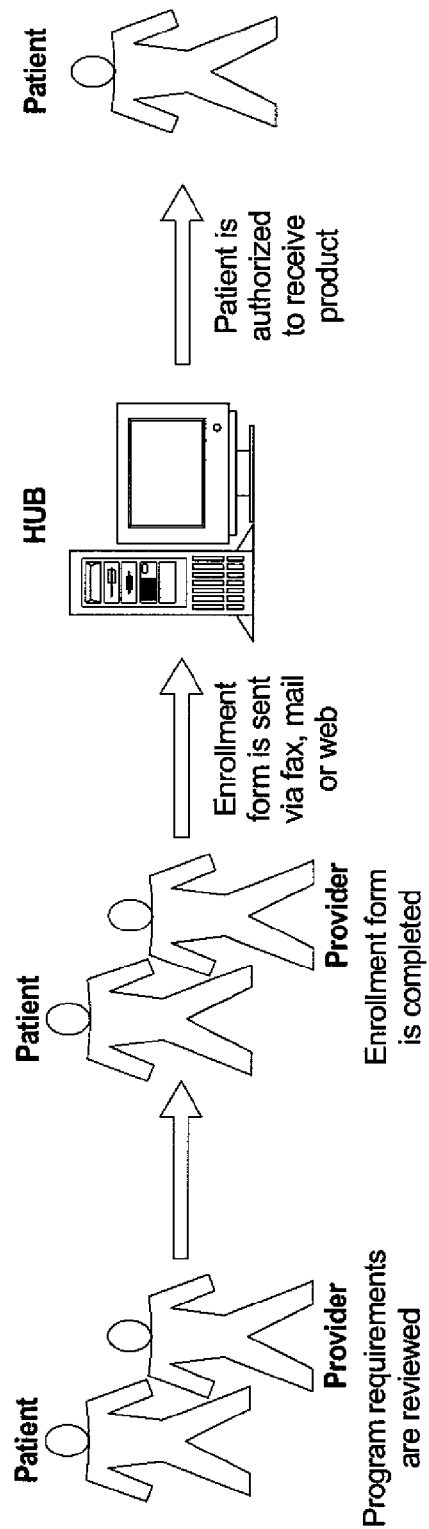
FIG. 15 is a flow diagram showing an example of a process for patient enrollment.

A flow diagram showing an example of a process for patient enrollment is illustrated in FIG. 15. In this example, the system permits and/or facilitates a patient and/or a health care provider to review the program requirements. The system permits and/or facilitates the patient and/or the healthcare provider to then complete a patient enrollment form (which may also include prescription information), agree to participate in the program, and submit the patient enrollment form to the system (e.g., via web, fax, or mail). The system then verifies that the submitted information is complete (e.g., includes information in the address field) and accurate (e.g., the address is current for this patient). If the information is complete and accurate, the patient is registered in the system database. Subsequently (or effectively simultaneously), the patient is authorized to receive prescriptions from doctors enrolled in the system.

Figure 16:
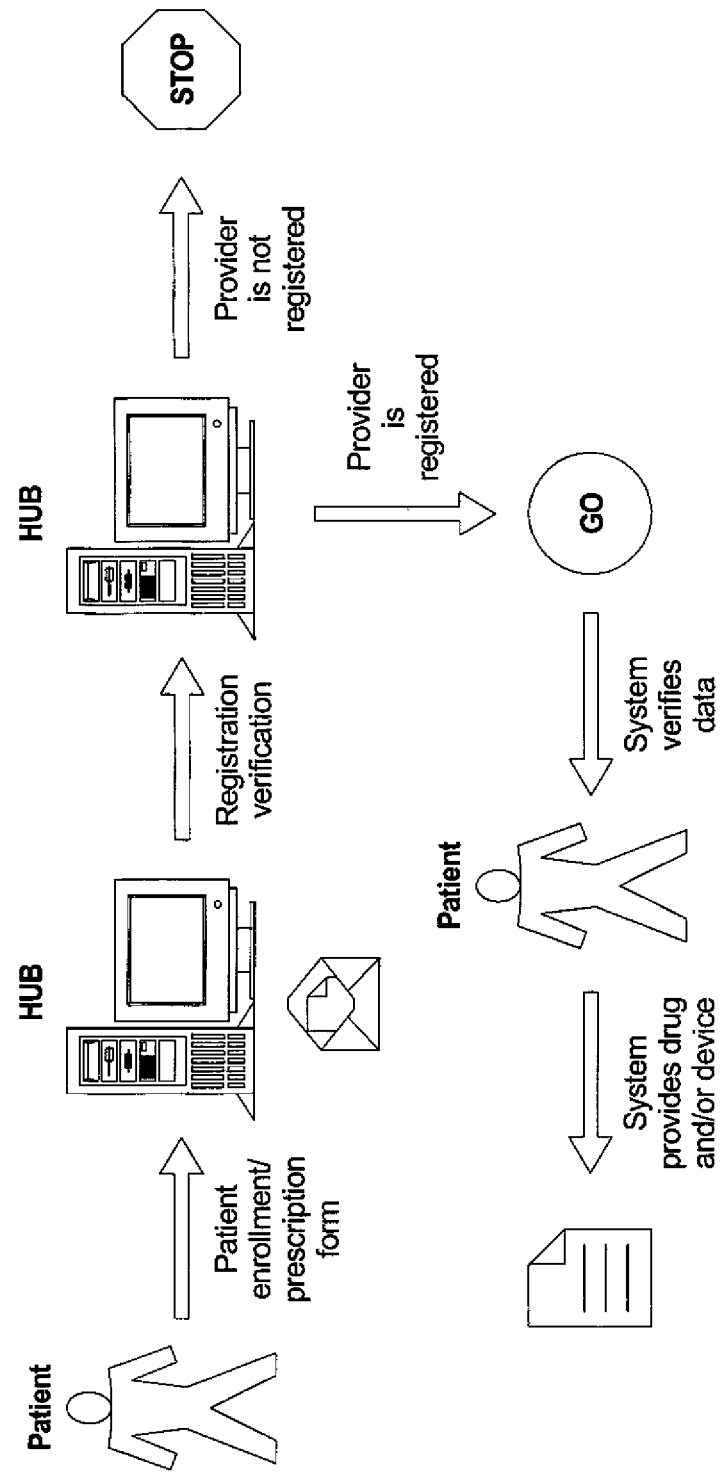
FIG. 16 is a flow diagram showing an example of a process for prescription fulfillment.

A flow diagram showing an example of a process for prescription fulfillment is illustrated in FIG. 16. In this example, a patient enrollment form and prescription are received by the system. The system verifies the healthcare provider is registered. In addition, the system either registers the patient or verifies the patient was previously registered. If the patient and the provider are both registered in the system, the system optionally performs a benefit investigation and may contact the patient to discuss program requirements and confirm the patient's shipping address. Subsequently, the prescription drug and optionally one or more outcome data collection devices are provided (e.g., shipped) to the patient. In addition, the patient's insurance claim may be processed.

The aforementioned systems and processes may be used for a variety of medical fields and diseases or conditions, such as for example cardiovascular disease (e.g., hypertension, high cholesterol), endocrinology and/or metabolic disease (e.g., Type 2 diabetes, obesity), inflammatory disease and/or rheumatology (e.g., rheumatoid arthritis, osteoarthritis), oncology (e.g., breast cancer, colon cancer), neurologic disease (e.g., Alzheimer's, Parkinson's), gastroenteric disease (e.g., inflammatory bowel disease), autoimmune disease (e.g., Type 1 diabetes, multiple sclerosis), dermatologic disease (e.g., psoriasis, dermatitis), infectious disease (e.g., influenza, hepatitis), ophthalmologic disease (e.g., retinopathy, uveitis), nephrology (e.g., chronic kidney disease), otolaryngology (e.g., otitis media, sinusitis), pulmonary disease (e.g., chronic obstructive pulmonary disease, pulmonary fibrosis), orthopedic disease (e.g., osteoporosis), hematologic disease (e.g., leukemia), allergy (e.g., allergic rhinitis), gynecological disease (e.g., endometriosis), urologic disease and psychiatric disease, and as noted in Table 1 below

TABLE 1

| Indicated medical condition | Drug (type) | Measurement (e.g., device and/or observation) | Outcome information |
|---|---|---|---|
| Hypertension | ACE inhibitor | Blood pressure monitor | Change (e.g., decrease) in blood pressure |
| | | Observation, blood test, imaging (e.g., MRI, CT scan) | Occurrence of a cardiovascular events (e.g., myocardial infarction, stroke, death) |
| Type 2 diabetes | DPP-4 inhibitor | Blood glucose monitor | Change (e.g., decrease) in blood sugar and/or HBA1c |
| | | Observation, blood test, imaging (e.g., MRI, CT scan) | Occurrence of a cardiovascular events (e.g., myocardial infarction, stroke, death) |
| High cholesterol | Statin | Cholesterol test kit | Change (e.g., decrease) in total cholesterol |
| | | Observation, blood test, imaging (e.g., MRI, CT scan) | Occurrence of a cardiovascular events (e.g., myocardial infarction, stroke, death) |
| Alzheimer's disease | Cholinesterase inhibitor | Imaging (e.g., MRI, CT scan) | Change (e.g., delay) in worsening of condition |
| Rheumatoid arthritis | TNF-alpha inhibitor | X-ray | Change (e.g., improvement, delay in worsening) in joint |
| Breast cancer | Taxane | Radiologic assessment | Change (e.g., increase) in tumor response rate |
| Chronic obstructive pulmonary disorder (COPD) | Beta-2 agonist | Self-evaluation | Change (e.g., improvement) in exercise persistence and/or shortness of breath |
| Atopic dermatitis | Corticosteroid | Self-evaluation | Change (e.g., improvement) in skin condition |
| Pain | NSAIDS | Quality of life survey | Patient observation of pain; Change in quality of life score |

In summary, persons of ordinary skill in the art will readily appreciate that methods and apparatus for obtaining and using outcome information associated with a prescription drug, have been provided. The foregoing description has been presented for the purposes of illustration and description. It is not intended to be exhaustive or to limit the invention to the exemplary embodiments disclosed. Many modifications and variations are possible in light of the above teachings. It is intended that the scope of the invention be limited not by this detailed description of examples, but rather by the claims appended hereto.

The invention claimed is:

1. A computer-implemented method of prescribing a prescription drug indicated for use in treating an indicated medical condition and for monitoring and tracking patient response to use of said prescription drug by a patient diagnosed with said indicated medical condition, said method comprising the steps of:

(a) electronically receiving and storing, in a database, data concerning an indicated medical condition;

(b) electronically receiving and storing, in a database, data concerning a prescription drug indicated for use treating said indicated medical condition;

(c) electronically receiving and storing, in a database, one or more outcome data types pre-selected by one or more medical professionals; said one or more outcome data types being associated in said database with said indicated medical condition and said prescription drug; said one or more outcome data types correlating the effect of use of said prescription drug by a patient diagnosed with said indicated medical condition to the treatment of said indicated medical condition in said patient;

(d) electronically receiving and storing, in a database, data concerning an outcome information monitoring device; said outcome information monitoring device being capable of obtaining patient outcome information corresponding to said one or more outcome data types;

(e) electronically receiving doctor registration data from a doctor, and storing said doctor registration data in a database; said doctor registration data including information concerning said doctor;

(f) electronically receiving patient registration data from at least one of said doctor and said patient, and storing said patient registration data in a database; said patient registration data including information concerning said patient;

(g) electronically receiving prescription data from said doctor, and storing said prescription data in a database; said prescription data including information concerning said patient, said patient's indicated medical condition, and said prescription drug indicated for use in treating said patient's indicated medical condition;

(h) electronically receiving payer data received from at least one of said doctor, said patient and a payer, and storing said payer data in a database; said payer data including information concerning a payer, said patient, and said prescription drug;

(i) electronically verifying that doctor registration data is stored in said database of step (e) for said doctor providing said prescription data of step (g);

(j) if said doctor registration data is verified in step (i), causing said prescription drug to be provided to said patient as indicated by said patient's patient registration data stored in said database of step (f); said prescription drug being provided directly to said patient from a single prescription drug fulfillment source one or a plurality of times, as indicated by said prescription data stored in said database of step (g);

(k) causing an outcome information monitoring device to be provided to said patient based on said outcome information monitoring device data stored in said database of step (d);

(l) electronically receiving fulfillment data, and storing said fulfillment data in a database; said fulfillment data including information concerning fulfillment of said prescription drug by said single prescription drug fulfillment source of step (j); and (m) electronically receiving, from said patient, patient outcome information corresponding to said one or more outcome data types and obtained by said outcome information monitoring device provided to said patient in step (k), and storing said patient outcome information in a database;

said steps (a)-(m) being implemented in a computer system comprising one or more processors configured to execute one or more computer programs; and said fulfillment data and said patient outcome information being available to at least one of said doctor, said patient and said payer through one or more electronic interfaces of said computer system to monitor and track patient compliance to said prescription data and patient response to said prescription drug, and to correlate said fulfillment data to said patient response to said prescription drug, and wherein said computer system compares said fulfillment data of step (l) to said prescription data of step (g) to determine patient compliance, and electronically notifies at least one of said doctor, said patient and said payer if said patient is not compliant.

2. A computer-implemented method according to claim 1, further comprising the steps of electronically storing in said computer system, in a database, data concerning a second prescription drug indicated for use in treating said patient's indicated medical condition, said second prescription drug being different from said prescription drug indicated by said prescription data; determining in said computer system if said second prescription drug is indicated for use by said patient on the basis of said patient outcome information; and electronically communicating said determination to said doctor.

3. A computer-implemented method according to claim 1, wherein said step of electronically receiving said prescription data from said doctor occurs before said step of electronically receiving said patient registration information; occurs after said step of receiving said patient registration information; or occurs at the same time as said step of receiving said patient registration information.

4. A computer-implemented method according to claim 1, further comprising: the steps of electronically receiving a query in said computer system; and electronically delivering, in said computer system, a report based on said patient outcome information in response to said query.

5. A computer-implemented method according to claim 4, wherein said query comes from at least one of said doctor, said payer, and said patient.

6. A computer-implemented method according to claim 4, wherein said report includes a comparison of said second prescription drug to said prescription drug indicated by said prescription data.

7. A computer-implemented method according to claim 1, wherein said one or more outcome data types are selected from the group consisting of: change in blood pressure; occurrence of cardiovascular events; change in at least one of blood sugar and HBA1c; change in total cholesterol; change in worsening of condition; change in joint function; change in tumor response rate; change in at least one of exercise persistence and shortness of breath; change in skin condition; change in patient observation of pain; and change in quality of life score.

8. A computer-implemented method according to claim 1, wherein said indicated medical condition is selected from the group consisting of: hypertension; type 2 diabetes; high cholesterol; Alzheimer's disease; rheumatoid arthritis; breast cancer; chronic obstructive pulmonary disorder (COPD); atopic dermatitis; and pain.

9. A computer-implemented method according to claim 1, wherein said prescription drug is a drug selected from the group consisting of: ACE inhibitors; DPP-4 inhibitors; statins; cholinesterase inhibitors; TNF-alpha inhibitors; taxanes; beta-2 agonists; corticosteroids; and NSAIDS.

10. A computer-implemented method according to claim 1, wherein said outcome information monitoring device is selected from the group consisting of: a blood pressure monitor; a blood glucose monitor; and a cholesterol test kit.

11. A computer-implemented method according to claim 1, wherein said computer system comprises a doctor client device, a patient client device, a payer client device and one or more database servers, each of which is different from and in network communication with each other; said prescription data being electronically received from said doctor client device and said patient outcome information being electronically received from said patient client device; and each of said databases being stored on said one or more database servers.

12. A computer-implemented method according to claim 11, wherein said indicated medical condition is hypertension; said prescription drug indicated for use in treating said hypertension is an ACE inhibitor; said one or more outcome data types associated with said hypertension is at least one of change in blood pressure and occurrence of cardiovascular events; and said outcome information monitoring device is a blood pressure monitor.

13. A computer-implemented method according to claim 11, wherein said indicated medical condition is Type 2 diabetes; said prescription drug indicated for use in treating said Type 2 diabetes is a DPP-4 inhibitor; said one or more outcome data types associated with said Type 2 diabetes is change in at least one of blood sugar and HBA1c, and occurrence of cardiovascular events; and said outcome information monitoring device is a blood glucose monitor.

14. A computer-implemented method according to claim 11, wherein said indicated medical condition is high cholesterol; said prescription drug indicated for use in treating said high cholesterol is a statin; said one or more outcome data types associated with said high cholesterol is at least one of change in total cholesterol and occurrence of cardiovascular events; and said outcome information monitoring device is a cholesterol test kit.

15. A computer-implemented method according to claim 2, wherein the dosage of said second prescription drug is different from the dosage of said prescription drug indicated by said prescription data.

16. A computer-implemented according to claim 2, wherein the active ingredient of said second prescription drug is different from the active ingredient of said prescription drug indicated by said prescription data.

17. A computer-implemented method according to claim 2, wherein the active ingredient of said second prescription drug is the same as the active ingredient of said prescription drug indicated by said prescription data; said active ingredient of said second prescription drug being at a different dosage level that said same active ingredient of said prescription drug indicated by said prescription data.

18. A computer-implemented method according to claim 2, wherein the frequency of consumption of said second prescription drug is different from the frequency of consumption of said prescription drug indicated by said prescription data.

19. A computer-implemented method according to claim 2, wherein said second prescription drug and said prescription drug indicated by said prescription data are taken by said patient at different times of the day.

20. A computer-implemented method according to claim 2, wherein said second prescription drug and said prescription drug indicated by said prescription data are administered to said patient together as a fixed dose combination or separately as a combination monotherapy.

21. A computer-implemented method according to claim 2, further comprising the step of electronically comparing, in said computer system, the efficacy of said prescription drug indicated by said prescription data administered in the absence of said second prescription drug, to the efficacy of said prescription drug indicated by said prescription data administered in combination with said second prescription drug.

* * * * *